United States Patent [19]

Cheminal et al.

[11] Patent Number: 4,647,706

[45] Date of Patent: Mar. 3, 1987

[54] PROCESS FOR THE SYNTHESIS OF 2,2,2-TRIFLUOROETHANOL AND 1,1,1,3,3,3-HEXAFLUOROISOPROPANOL

[75] Inventors: Bernard Cheminal, Lyons; Henri Mathais, Saint Didier au Mont d'Or; Marc Thomarat, Pierre-Benite, all of France

[73] Assignee: Atochem, France

[21] Appl. No.: 755,696

[22] Filed: Jul. 16, 1985

[30] Foreign Application Priority Data

Jul. 18, 1984 [FR] France .................. 84 11383

[51] Int. Cl.$^4$ .............................. C07C 31/34
[52] U.S. Cl. ..................... 568/842; 502/162
[58] Field of Search ......................... 568/842

[56] References Cited

U.S. PATENT DOCUMENTS 3,607,952  9/1971  Lee ........................ 568/842
3,702,872  11/1972  Regan .................... 568/842
3,714,271  1/1973  Regan .................... 568/842

FOREIGN PATENT DOCUMENTS 2133126  11/1972  France .................... 568/842

0204142  11/1984  Japan ..................... 568/842
2087383  5/1982  United Kingdom ........... 568/842

OTHER PUBLICATIONS

Gambaryan et al, Angewandte Chemie, Int. Ed, 5 (11) pp. 947–948 (Nov. 1966).

*Primary Examiner*—Howard T. Mars
*Attorney, Agent, or Firm*—Brooks Haidt Haffner & Delahunty

[57] ABSTRACT

A process for producing 2,2,2-trifluoroethanol or 1,1,1,3,3,3-hexafluoroisopropanol which comprises hydrogenating a fluoro compound having the formula

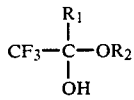

wherein $R_1$ is hydrogen or $CF_3$ and $R_2$ is hydrogen or a straight- or branched-chain alkyl group, which can also be fluoro-substituted, in the liquid phase in the presence of a palladium-on-activated-carbon catalyst, and if desired a tertiary amine co-catalyst.

13 Claims, No Drawings

PROCESS FOR THE SYNTHESIS OF 2,2,2-TRIFLUOROETHANOL AND 1,1,1,3,3,3-HEXAFLUOROISOPROPANOL

BACKGROUND OF THE INVENTION

The present invention relates to the preparation of 2,2,2-trifluoroethanol and 1,1,1,3,3,3-hexafluoroisopropanol, and more particularly, it relates to the preparation of such fluorinated alcohols by hydrogenolysis of hydrates or hemiacetals of the corresponding polyfluorinated carbonyl compounds.

A major commercial source of fluorinated primary alcohols such as 2,2,2-trifluoroethanol is based on the reduction of the corresponding acid (trifluoroacetic acid in this case) or of a derivative (the ester, acid chloride, anhydride, or amide) with hydrogen in the presence of a catalyst generally chosen from the precious metals group, such as rhodium, ruthenium, platinum, or palladium. This trifluoroethanol is used in a wide variety of applications including energy recovery, in absorption type heat pumps; pharmaceutical products, such as anaesthetics; and as solvents.

The hydrogenation of trifluoroacetic anhydride is shown in U.S. Pat. No. 4,255,594 and that of trifluoroacetic acid in U.S. Pat. No. 4,273,947; hydrogenation of esters of trifluoroacetic acid shown in European Pat. No. 36,939; hydrogenation of trifluoroacetamide shown by M. Gilman, J.A.C.S., 70, 1281-2 (1948); and hydrogenolysis of trifluoroacetyl chloride as shown in U.S. Pat. No 3,970,710 are some of the usual methods employed to prepare fluorinated primary alcohols. In addition to the disadvantage of catalyst activity decreasing with the passage of time, these processes share the economic disadvantage of resorting to an oxidation of the usually chlorine-containing starting materials to obtain the acid or one of its derivatives, followed by a reduction of this acid to the alcohol. This additional step very severely impairs the profitability of these processes.

Another group of processes calls for hydrogenating trifluoroacetaldehyde (called "fluoral" hereinafter) or one of its derivatives. The yield obtained by liquid phase hydrogenation (80° C. at 95 bars) of fluoral hydrate over Raney nickel as shown in French Pat. No. 1,399,290 is mediocre. The catalyst life and the purity required in the starting material are not stated. There is a risk of a side reaction, known as the haloform reaction:

CF$_3$CHO+NaOH→CHF$_3$+HCOONa (1)

with the sodium hydroxide which is always absorbed on the catalyst.

U.S. Pat. No. 2,982,789 describes gas-phase hydrogenation of fluoral hydrochloride, CF$_3$CH(Cl)OH, obtained from a first hydrogenolysis step (the Rosenmund reaction) of trifluoroacetyl chloride on a palladium catalyst. The fluoral hydrogenation catalyst, which consists of copper chromite deposited on calcium fluoride, and whose behaviour with the passage of time is not mentioned, operates at about 250° C. and permits the intermediate fluoral to be converted only incompletely (approximately 60–65%). Additionally, recycling of the unconverted fluoral hydrochloride is a very risky operation because of its thermal instability, the decomposition:

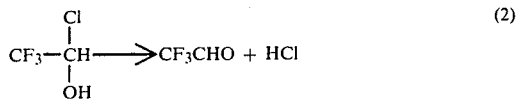

being promoted even at 30° C. by a temperature rise or a pressure reduction. Finally, U.S. Pat. No. 3,468,964 shows gas phase hydrogenation of fluoral in the presence of a catalyst containing palladium deposited on alumina, at low temperature (peak temperature: 140° C.). The moderate yield of trifluoroethanol (86%) and the need to regenerate the catalyst very frequently at 200° C. in pure oxygen, together with the extreme difficulty of handling fluoral in the pure state, due to polymerization, make the process unattractive.

French Pat. No. 2,027,172 relates to a process for gas phase hydrogenation of perhaloketones over a palladium-based catalyst deposited on activated charcoal and particularly describes catalytic hydrogenation of hexafluoroacetone (CF$_3$COCF$_3$) to yield 1,1,1,3,3,3-hexafluoroisopropyl alcohol. The yield obtained (75%) and the difficulty of handling the starting material (b.p.: −27.4° C./760 torr) make the process uneconomical. French Pat. No. 2,479,803 carries out a gas phase catalytic hydrogenation of hexafluoroacetone to 1,1,1,3,3,3-hexafluoroisopropanol over a nickel-based catalyst. The catalyst life is not rated for a continuous operation time longer than 20 hours and, above all, this process requires the use of a pure starting material, which is difficult to obtain in the case of hexafluoroacetone. French Pat. No. 1,361,260 carries out the gas phase catalytic hydrogenation of hexafluoroacetone over a catalyst based on copper chromite. The yields of 1,1,1,3,3,3-hexafluoroisopropanol are mediocre (approximately 40%) for a partial conversion (83%) of the ketone used. This entails difficult and costly recycling.

French Pat. No. 2,133,126 describes a liquid phase process for the hydrogenation of perfluoroacetone to hexafluoroisopropanol in the presence of a catalyst containing palladium activated with an inorganic base of the alkali metal type. The catalyst so activated makes it possible to obtain partial conversion (80 to 86%) of the starting ketone, but the hydrogenation times are long (approximately seven hours) and the hexafluoroacetone employed must be purified, which calls for a preliminary distillation at elevated pressure and complicates the process. The catalyst life is not specified.

French Pat. No. 2,493,831 shows a gas phase process for hydrogenating hexafluoroacetone hydrate in the presence of a catalyst based on nickel or palladium, excluding ruthenium or platinum. This process has a major disadvantage in that it is absolutely necessary to use a ketone hydrate which is particularly pure and refined by means of a complex method which is the subject of U. K. Pat. No. 2,086,891. This imperative requirement of refining the starting material to a high degree of purity makes the process for producing 1,1,1,3,3,3-hexafluoroisopropanol considerably more complicated.

Finally, Japanese published application 83/88,330 describes a process for the preparation of 1,1,1,3,3,3-hexafluoroisopropanol from hexafluoroacetone in the gaseous, or optionally in liquid, phase in the presence of a catalyst based on rhodium deposited on activated charcoal. Its principal disadvantage lies in the use of a very costly catalyst. In addition, the indication of a very slight drop in yield between the third and the fourth hour of operation (Example 2) from 100% to 98% leads to reservations concerning the actual behaviour of the catalyst with the passage of time. In fact, if this drop continues at the same rate, it means that the residence time must be doubled after every 50 hours of operation; this is not economically feasible.

THE INVENTION

The present invention makes it possible to overcome these disadvantages by offering a simple, flexible, and particularly economical method for providing 2,2,2-trifluoroethanol or 1,1,1,3,3,3-hexafluoroisopropanol, even when using a crude starting material which is easy to prepare and to handle, and without detriment to catalyst life, to yield, or to productivity.

Briefly, the process according to the present invention comprises subjecting a compound of the general formula:

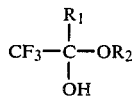

(I)

in which $R_1$ is a hydrogen atom or a trifluoromethyl radical and $R_2$ is a hydrogen atom or a straight- or branched-chain alkyl group containing from one to eight carbon atoms, which latter group can also be partly fluorinated, to a liquid phase hydrogenolysis in the presence of a palladium-containing catalyst deposited on activated charcoal. In certain embodiments, a tertiary aliphatic amine co-catalyst can also be used.

The hydrate or hemiacetal compounds of formula (I), employed as starting materials in the process according to this invention, can be obtained, in the crude state, in a known manner by reacting water, when $R_2$ is hydrogen, or an alcohol, when $R_2$ is optionally a substituted alkyl, with fluoral ($R_1$ is H) or hexafluoroacetone ($R_1$ is $CF_3$) according to the following reaction scheme:

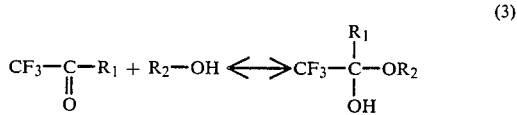

(3)

The alkyl radical $R_2$ can contain up to eight carbon atoms. In certain preferred embodiments, $R_2$ is methyl, ethyl, n-propyl, isopropyl, n-butyl, sec-butyl, n-hexyl, 2-ethylhexyl, 2,2,2-trifluoroethyl, or 1,1,1,3,3,3-hexafluoro-2-propyl.

The thermal stability of the compounds obtained depends principally on the temperature, the pressure, and the chemical nature of the compounds. In general, the hydrates ($R_2$ is H) are stable but difficult to purify by distillation. The hemiacetals ($R_2$ is alkyl) are proportionately more stable, the lower the number of carbon atoms in the $R_2$ alkyl group. Their purification frequently requires distillation under reduced pressure (200 torr) and a short residence time, such as obtained in falling film evaporation. To give some examples, the crude hemiacetal $CF_3$—CH(OH)—$OCH_3$ is stable and can be distilled (boiling point: 96° C./760 torr) at atmospheric pressure without decomposition. Consequently, it can be separated from chlorinated compounds (which are heavier) and from hydrochloric acid. A product which assays at 99.9% or higher purity is then obtained when an excessive residence time (approximately a few minutes) in the distillation boiler is avoided. On the other hand, the hemiacetal $CF_3$—CH(OH)—$OCH_2CF_3$, which is highly unstable, cannot be purified by distillation. Nevertheless, according to the present invention, it can be employed as such in the crude state, that is, in the form of a mixture containing from one to ten mole percent of chlorohemiacetal $CF_2Cl$—CH(OH)—$OCH_2CF_3$, from 0.1 to ten mole percent of dichlorohemiacetal $CFCl_2$—CH(OH)—$OCH_2CF_3$, and from one to ten mole percent of hydrochloric acid.

The palladium content of the catalyst employed in the process of the present invention can be from 0.1 to ten percent by weight. In certain preferred embodiments, a catalyst containing approximately five percent palladium is used. The quantity of catalyst to be used depends on its palladium content. For a commercial catalyst containing five percent palladium, the quantity of catalyst is from 0.2 to 2.5%, and in preferred embodiments, from 0.3 to one percent, based on the weight of the crude hydrate or hemiacetal substrate used.

The catalyst can be used with or without preliminary activation in the reactor before the hydrogenolysis. An optional activation can be carried out, for example, at a temperature of between 25° and 100° C. under a hydrogen pressure of 35 to 45 bars.

After each hydrogenolysis, the catalyst can usefully be separated from the reaction mixture by decanting and then filtration, followed by one or more washes with water or with the pure alcohol synthesized in the process. It can also be left (preferably for less than 48 hours) in contact with the reaction mixture, allowed to separate by gravity, and then the reaction mixture can be separated by draining under a hydrogen atmosphere. The following run can be restarted over the same catalyst charge.

The reactants, including if desired the co-catalyst, can be introduced with the catalyst at the beginning of the reaction. However, to avoid excessively fast deactivation of the catalyst with the passage of time, it is preferred to introduce the mixture of the reactants gradually, in a mixture containing the alcohol produced in the preceding synthesis or purified alcohol and catalyst. Deactivation of the catalyst can be observed by using X-ray diffraction to determine the size of palladium crystallites formed during the reaction. The rate of hydrogenolysis is, in fact, inversely proportional to the square of the diameter of the active particles of catalyst. Since the growth of these particles due to a coalescence phenomenon corresponds to a reduction in activity of the catalytic species, to avoid accelerating the deactivation, it is preferred to use an amorphous, finely divided catalyst, whose primary particles (or crystallites) have a diameter less than or equal to 4 nm. The diameter is preferably 2 to 4 nm in preferred embodiments.

The hydrogenolysis can be carried out at a temperature of from 80° to 130° C., preferably 90° to 110°, and at a pressure of from 20 to 50 bars, preferably 35 to 45 bars.

In a preferred embodiment of the process of this invention, the reactants (substrate) and, if desired the co-catalyst, are added gradually to the hydrogenolysis reactor. The addition time is from 0.2 to five hours, preferably from 0.75 to 1.25 hours. To prevent excessively fast deactivation of the catalyst, it is particularly preferred that the reactant addition rate correspond as exactly as possible to the rate of hydrogenolysis. A highly preferred regulating system for achieving this involves controlling the output of the injection pump by the hydrogen consumption (which is itself related to hydrogen flow rate or pressure). In this way, in step with the slow deactivation of the catalyst with the passage of time, the slight loss in activity can be compensated by correspondingly lengthening the addition period for the reactants. This considerably increases the flexibility of the process, as well as its economy.

The use of a tertiary aliphatic amine co-catalyst is not absolutely essential, but it is nevertheless very desirable. It makes it possible not only to facilitate the opening of the hemiacetal but also to trap foreign ions (more particularly chlorides and fluorides) which may cause an uncontrolled acceleration of the catalyst crystallization and consequent catalyst deactivation.

The use of a co-catalyst is particularly convenient when the substrate is a stable hemiacetal formed with one- or two-carbon aliphatic alcohols, e.g., methanol. In the majority of cases, co-catalyst removal from the reaction medium by distillation, after hydrogenolysis, and its recycling in a subsequent operation are easily accomplished. A material with a suitable boiling point is used for this purpose. In addition, the basic nature of the co-catalyst lends itself readily to neutralization (if need be at the start of distillation) in the form of ammonium salts, which are stable and can be separated by distillation. Distillation is followed by recovery with the aid of a strong base, such as sodium hydroxide or the like, at the end of the distillation.

The tertiary aliphatic amines to be employed as co-catalysts have the formula:

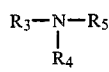
(II)

in which $R_3$, $R_4$, and $R_5$ can be the same or different and represent an alkyl group which can if desired be hydroxy-substituted. Preferred co-catalysts include trimethylamine, tri-n-propylamine, tributylamine, dimethylethylamine, dimethylethanolamine, and triethanolamine. An especially preferred co-catalyst is triethylamine.

The quantity of co-catalyst can be varied over wide limits, depending on the purity of the substrate (the hydrate or hemiacetal) subjected to the hydrogenolysis. It is desirable to start with a substrate which is as pure as possible, but this is not always feasible. A less effective fluorination catalyst results in a higher content of chlorinated products, with a secondary reaction of the alcohol making it necessary to absorb the carbonyl derivative at a low temperature, which increases the solubility of hydrochloric acid, chlorinated and fluorinated hydrates which are inseparable by distillation. The quantity of co-catalyst is from none to the number of moles of chlorinated by-products present in the crude starting material, calculated in H+ equivalents and increased by a molar excess of from 5 to 500%.

The vehicle employed in the process can be any usual organic solvent, such as aliphatic ketones, ethers, glycols, chlorinated solvents, and the like. In practicing this invention, the preferred vehicles are the polyfluorinated alcohol, that is, the 2,2,2-trifluoroethanol or 1,1,1,3,3,3-hexafluoroisopropanol produced by the process of the invention. It is also possible to use an aliphatic alcohol $R_2OH$, where $R_2$ has the same meaning as above. The quantity of vehicle to be employed can vary from none to 100%, based on the weight of the substrate used. The amount of vehicle depends on the geometry of the hydrogenolysis reactor to ensure excellent mixing and on the required productivity.

The process according to the invention can be carried out in a conventional apparatus, that is, an autoclave agitated by a suitable mechanical means, capable of operating at a pressure of 50 bars, fitted with a means for draining the catalyst suspension and with the essential attachments, such as filter, pumps, hydrogen pressure control, and the like. Corrosion protection by a suitable internal coating is not essential, but can be utilized to prevent the reaction from being inhibited by foreign ions, such as ferrous, chromium, nickel, and the like.

The hydrogenolysis according to the invention can also be carried out in a continuous liquid phase on a fixed bed of catalyst.

The polyfluorinated alcohol produced is isolated and purified by conventional techniques such as distillation and drying on a molecular sieve. Its purity can be determined by gas phase chromatography.

All parts, percentages, proportions, and ratios herein are by weight unless otherwise stated.

The following Examples are given to illustrate embodiments of the invention as it is presently preferred to practice it. It will be understood that these Examples are illustrative, and the invention is not to be considered as restricted thereto except as indicated in the appended claims.

The catalyst employed in these Examples is one made by the Engelhard Corp. It contains five per cent palladium deposited on activated carbon and is in the form of a fine powder, all the particles of which have a diameter greater than 0.5 micrometers. In the tables, the term C2 denotes the compounds $CF_xCl_{3-x}CHO$ (x being 1, 2 or 3).

EXAMPLE I

Hydrogenolysis of Crude $CF_3$—$CH(OH)$—$OCH_2CH_3$

A 0.1-liter autoclave fitted with a magnetic stirring system is charged successively with 0.51 g of catalyst, and then with 51 g of crude hemiacetal containing (in moles) 94% of $CF_3$—$CH(OH)$—$O$—$CH_2$—$CH_3$ and 6% of $CF_2Cl$—$CH(OH)$—$O$—$CH_2$—$CH_3$, corresponding, respectively, to 0.332 mole and 0.021 mole, the dissolved hydrochloric acid being equivalent to 0.00436 mole, and the hydrofluoric acid to 0.00018 mole. Then, 4.7 g of pure triethylamine (0.0465 mole) is added, which is an 82% molar excess, based on the theoretical. The reactor is closed, the entrapped air is purged with nitrogen and then a slight hydrogen pressure is introduced, after which the reaction mixture is heated to about 120° C while being stirred. The hydrogen pressure is adjusted to 43–44 bars.

The pressure drop attributable to the consumption of hydrogen is then compensated by successive additions of hydrogen between 33 and 43 atmospheres. Once hydrogen absorption has ended, the reaction mixture is cooled rapidly and then, after it has been degassed into a container maintained at about -196° C. with liquid nitrogen, the reactor is opened. The reaction product mixed with the catalyst is transferred into a container in which the catalyst suspension is allowed to separate by gravity. After the catalyst has separated, a sample of the hydrogenolysis product is analysed. The pH of an aqueous solution is noted and the chloride and fluoride ions formed during the reaction are determined by inorganic analysis.

The same catalyst charge is then recycled during two successive runs under the same operating conditions, in the same apparatus and with the same substrate and the same co-catalyst. Table I collates the results obtained during this series of runs.

TABLE I

| Run No. | Reaction Time (hrs and min) | Degree of Conversion to $CF_3CH_2OH$ % | pH | Cl-formed (per 100 moles of $C_2$) | F-formed (per 100 moles of $C_2$) |
|---|---|---|---|---|---|
| 11 | 1 h | 100 | 10 | 5.25 | 0.69 |
| 12 | 2 h 25 m | 100 | 9.9 | 4.75 | 0.58 |
| 13 | 6 h 20 m (incomplete reaction) | 78 | 9.1 | 5.09 | 1.14 |

EXAMPLE II

Hydrogenolysis of Crude $CF_3$—CH(OH)—$OCH_2CH_3$

Three runs are carried out by operating as in Example I, with the following differences: The crude hemiacetal employed contains 96 mole percent of $CF_3$—CH(OH)—$OC_2H_5$, 4 percent of $CF_2Cl$—CH(OH)—$OC_2H_5$, 0.00183 mole of HCl and 0.00274 mole of HF; only 0.17 g of catalyst is employed and this charge is renewed at each operation; and the quantity of triethylamine is varied: 0.0247 mole for Run 21, 0.0455 mole for Run 22 and 0.0860 mole for Run 23.

Table II presents the results obtained during this series of runs.

Comparison of these results with those obtained in Example I makes it possible to assess the respective effects of the catalyst and of the co-catalyst on the course of the reaction.

TABLE II

| Run No. | Moles of Co-Catalyst | Reaction Time (hrs and min) | Degree of Conversion to $CF_3CH_2OH$ % | pH | Cl-formed (per 100 moles of $C_2$) | F-formed (per 100 moles of $C_2$) |
|---|---|---|---|---|---|---|
| 21 | 0.0247 | 4 h 30 m (incomplete reaction) | 76 | 11.47 | 6.28 | 0.32 |
| 22 | 0.0455 | 2 h 00 m | 100 | 10.0 | 6.25 | 0.70 |
| 23 | 0.0860 | 4 h 30 m | 100 | 10.62 | 6.53 | 0.93 |

EXAMPLE III

Hydrogenolysis of Crude $CF_3$—$CH(OH)_2$

The process is carried out as in Example I with 0.51 g of catalyst, 5.35 g of pure triethylamine (0.053 mole) and 43 g of crude fluoral hydrate having the following composition:

| $CF_3$—$CH(OH)_2$ | 0.337 mole |
|---|---|
| $CF_2Cl$—$CH(OH)_2$ | 0.022 mole |
| Dissolved HCl | 0.0095 mole |
| Dissolved HF | 0.0000688 mole |

After four hours at 120° C. under approximately 35 to 45 bars, the reaction is complete and the yield of 2,2,2-trifluoroethanol is quantitative. Analysis gives:
Cl—formed/(mole C2×100)=5.47
F—formed/(mole C2×100)=1.07

EXAMPLE IV

Hydrogenolysis of Crude $CF_3$—CH(OH)—O—$CH_2$—$CF_3$

This run is carried out as in Example I with 0.43 g of catalyst, 5.35 g of pure triethylamine (0.053 mole), and 59.4 g of crude hemiacetal having the following composition:

| $CF_3$—CH(OH)—O—$CH_2CF_3$ | 0.300 mole |
|---|---|
| $CF_2Cl$—CH(OH)—O—$CH_2CF_3$ | 0.018 mole |
| Dissolved HCl | 0.012 mole |
| Dissolved HF | 0.0003 mole |

After one hour at 120° C. and 35 to 50 bars, the degree of conversion to 2,2,2-trifluoroethanol is 100 per cent. The pH of an aqueous solution of the hydrogenolysis product is 9.7 and analysis gives:
Cl—formed/(mole C2×100) =7.26
F—formed/(mole C2×100)=0.60

A second run carried out with the catalyst originating from the preceding run produces the following results:

| Degree of conversion to $CF_3CH_2OH$ after 5 hours' reaction | 89% |
|---|---|
| pH | 6.0 |
| Cl-formed | 7.0 |
| F-formed | 0.72 |

EXAMPLE V

Hydrogenolysis of Crude $CF_3$—CH(OH)—$OCH_2CF_3$

The same autoclave as in Example I is charged with 20.9 g of pure 2,2,2-trifluoroethanol and 0.44 g of catalyst, and this mixture is then heated at 100° C. and a hydrogen pressure of 40 bars for 30 minutes to activate the catalyst.

While this temperature and hydrogen pressure are maintained, 1.82 g of triethylamine (0.018 mole) and 61 g of a crude hemiacetal having the following composition:

| $CF_3$—CH(OH)—O—$CH_2$—$CF_3$ | 0.292 mole |
|---|---|
| $CF_2Cl$—CH(OH)—O—$CH_2$—$CF_3$ | 0.008 mole |
| $CFCl_2$—CH(OH)—O—$CH_2CF_3$ | 0.0009 mole |
| Dissolved HCl | 0.0068 mole |
| Dissolved HF | 0.000017 mole | is introduced gradually over 72 minutes.

When the addition has ended, the hydrogen feed is continued until the end of the reaction, as evidenced by absence of hydrogen take-up.

After rapid cooling of the reaction mixture by plunging the reactor into liquid nitrogen, the catalyst is quickly recovered by opening the reactor and separating off the solid on a 0.5 micron filter. The catalyst is washed eight times with water and dried for 20 minutes at 200 torr and ambient temperature, then for two hours at one torr and ambient temperature, and finally for two hours at one torr and a temperature of about 95° C.

The catalyst treated in this way is then recycled during two other successive runs under the same operating conditions. Table III presents the results obtained in these three runs.

TABLE III

| Run No. | Reaction Time (hrs and min) | Degree of Conversion to CF₃CH₂OH % | pH | Mean Rate, Moles C₂/(hr × g-at. Pd) |
|---|---|---|---|---|
| 51 | 1 h 24 m | 100 | 10 | 1250 |
| 52 | 1 h 20 m | 100 | 9.9 | 1240 |
| 53 | 1 h 30 m | 100 | 9.9 | 1150 |

When account is taken of mechanical loss of catalyst (approximately five percent), the loss in catalyst activity during these three successive operations can be estimated at four percent, which is low.

EXAMPLE VI

Hydrogenolysis of Crude $CF_3—CH(OH)—O—CH_2CF_3$

Seven successive runs are carried out as follows in the same autoclave as in Example I.

Run No. 61

The reactor is charged with 20.9 g of pure 2,2,2-trifluoroethanol and 0.43 g of catalyst, and this mixture is heated for 30 minutes at 100° C. and a hydrogen pressure of 40 bars. A mixture of 1.82 g of triethylamine and 61 g of the same crude hemiacetal as in Example V is then gradually added over 72 minutes while the temperature is maintained at approximately 100° C. and the hydrogen pressure at 40 bars. After the addition, the hydrogen feed (35 to 45 bars) is continued to the end of the reaction, and then the reaction mixture is rapidly cooled by plunging the reactor into liquid nitrogen. The reaction mixture is thereafter left to separate by gravity for 20 hours, and the reaction liquid is withdrawn by means of a dip-tube which opens 8 mm above the bottom of the reactor.

Run No. 62

Run 61 is repeated, using the catalyst kept in the reactor at the end of the run.

Run No. 63

Run 61 is repeated using the catalyst kept in the reactor at the end of Run 62. In addition, after cooling, the mixture is left to separate by gravity for 75 hours before withdrawal takes place.

Run No. 64

Run 61 is repeated with the catalyst originating from Run 63. However, the reaction mixture is cooled slowly during approximately four hours and is then left to separate by gravity for 20 hours.

Run No. 65

Run 64 is repeated with the catalyst originating from that run.

Run No. 66

Run 64 is repeated with the catalyst originating from Run 65, but without activating it beforehand, that is, no heating at 100° C. under hydrogen pressure, before continuous addition of the reactants.

Run No. 67

Run 64 is repeated with the catalyst originating from Run 66, but with prior activation.

Table IV below presents the results obtained during these seven runs.

TABLE IV

| Run No. | Reaction Time (hrs and min) | Degree of Conversion to CF₃CH₂OH % | pH | Mean Rate, Moles C₂/(hr × g-at. Pd) |
|---|---|---|---|---|
| 61 | 1 h 30 m | 100 | 10 | 1400 |
| 62 | 1 h 24 m | 100 | 10 | 1390 |
| 63 | 1 h 24 m | 100 | 10.1 | 1390 |
| 64 | 1 h 55 m | 100 | 10.1 | 1210 |
| 65 | 2 h 15 m | 100 | 10.1 | 1147 |
| 66 | 3 h 10 m | 100 | 9.9 | 795 |
| 67 | 3 h 00 m | 100 | 9.5 | 1028 |

EXAMPLE VII

Hydrogenolysis of Pure $CF_3—CH(OH)—OCH_3$

The example I autoclave is charged with 20 g of pure 2,2,2-trifluoroethanol and 0.60 g of catalyst, and this mixture is activated by heating at 100° C. under a hydrogen pressure of 40 bars for 30 minutes. While this temperature and this hydrogen pressure are maintained, a mixture of 0.63 g of triethylamine and 54.6 g of pure hemiacetal $CF_3—CH(OH)—OCH_3$ (purity greater than 99.5%) is then added during one hour.

The catalyst is recovered as in Example V and is reused in three other runs carried out in the same manner.

Table V shows the results thus obtained.

TABLE V

| Run No. | Reaction Time (hrs and min) | Degree of Conversion to CF₃CH₂OH % | pH | Mean Rate, Moles C₂/(hr × g-at. Pd) |
|---|---|---|---|---|
| 71 | 1 h 20 m | 100 | 9.9 | 1371 |
| 72 | 1 h 35 m | 100 | 10.0 | 1237 |
| 73 | 1 h 32 m | 100 | 10.0 | 1200 |
| 74 | 1 h 55 m | 100 | 9.8 | 1032 |

EXAMPLE VIII

Hydrogenolysis of Pure $CF_3—CH(OH)—OCH_3$

This Example is carried out as in Example I, but with 0.43 g of catalyst, 0.455 g of triethylamine (4.5 10-3 mole) and 39 g of a hemiacetal having the following composition:

| | |
|---|---|
| $CF_3—CH(OH)—OCH_3$ | 99.2% (0.298 mole) |
| $CF_2Cl—CH(OH)—OCH_3$ | 0.1% (0.002 mole) |
| Other impurities | 0.7% |

After 30 minutes at 100° C. and 35 to 45 bars, the degree of conversion to 2,2,2-trifluoroethanol is 100%. The pH of an aqueous solution of the hydrogenolysis product is 9.7 and analysis shows:
Cl—formed/(mole C2×100): 0.26
F—formed/(mole C2×100): 0.10

After being separated by gravity outside the reactor, the catalyst charge is used for a second run carried out under the same conditions. After a five-hour reaction, the following results are obtained:

| | |
|---|---|
| Degree of conversion | Approx. 100% |
| pH | 8.9 |
| Cl- formed | 0.23 |

| -continued | |
| --- | --- |
| F- formed | 0.16 |

EXAMPLE IX

This run is carried out as in Example V, but with triethylamine replaced by the same molar proportion of dimethylethylamine. The results obtained are summarized in Table VI.

TABLE VI

| Run No. | Reaction Time (hrs and min) | Degree of Conversion to CF$_3$CH$_2$OH % | pH | Mean Rate, Moles C$_2$/(hr × g-at. Pd) |
| --- | --- | --- | --- | --- |
| 91 | 1 h 7 m | 100 | 9.6 | 1310 |
| 92 | 1 h 12 m | 100 | 9.7 | 1263 |
| 93 | 1 h 7 m | 100 | 9.8 | 1400 |

EXAMPLE X

Hydrogenolysis of Crude (CF$_3$)$_2$—C.9(OH)—OCH$_3$

The Example I reactor is charged with 21 g of hexafluoroisopropanol and 0.42 g of catalyst, and this mixture is heated at 100° C. and a hydrogen pressure of 40 bars for 30 minutes.

A mixture of 10.7 g (0.106 mole) of triethylamine and 56 g (0.275 mole) of a crude hemiacetal corresponding to the formula C$_4$H$_4$F$_{5.67}$Cl$_{0.33}$O$_2$ and containing 0.00325 mole of hydrochloric acid and 0.000225 mole of hydrofluoric acid is then introduced during about 70 minutes.

After six hours of reaction at 100° C. under 31 to 46 bars, the degree of conversion to hexafluoroisopropyl alcohol is near 100 percent and the following results are obtained:

Cl—formed/(mole C3×100): 25.5
F—formed/(mole C3×100): 18.8

What is claimed is:

1. A process for the preparation of 2,2,2-trifluoroethanol which comprises hydrogenating a fluoro compound having the formula:

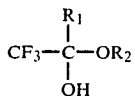

wherein R$_1$ is hydrogen and R$_2$ is hydrogen or a straight- or branched-chain alkyl group having from one to eight carbon atoms, in the liquid phase in the presence of a catalyst which is palladium deposited on activated carbon and of à tertiary aliphatic amine co-catalyst, the fluoro compound and co-catalyst being added gradually to a suspension of the palladium catalyst in a polyfluoro alcohol having the formula CF$_3$—CH(OH)—R$_1$.

2. A process according to claim 1 wherein R$_2$ is partially fluorinated.

3. A process according to claim 1 wherein the reaction mixture is rapidly cooled after the reaction has ceased and the catalyst is separated from the reaction mixture.

4. A process according to claim 3 wherein the catalyst separated from the reaction mixture is recycled to the process.

5. A process according to claim 4 wherein the catalyst is separated by filtration, washed with water, and dried before it is recycled.

6. A process according to claim 4 wherein the catalyst is separated by gravity, the reaction liquid is withdrawn, and the catalyst is kept in the same vessel.

7. A process according to claim 1 wherein the fluoro compound is used in the crude state.

8. A process according to claim 1 wherein the temperature is from 80° to 130°.

9. A process according to claim 1 wherein the pressure is from 20 to 50 bars.

10. A process according to claim 1 wherein the palladium content of the catalyst is from 0.1 to ten percent by weight.

11. A process according to claim 1 wherein the catalyst is activated prior to the reaction by treating the catalyst with hydrogen under a pressure of 35 to 45 bars at a temperature of from 25° to 100° C.

12. A process according to claim 1 wherein the quantity of catalyst is from 0.2 to 2.5 percent, based on the weight of the fluoro compound employed and expressed as five percent palladium content.

13. A process according to claim 1 wherein chlorinated by-products are present with the fluoro compound and a tertiary amine co-catalyst is used in an amount of from zero to the number of moles of the chlorinated by-products, calculated as hydrogen ion equivalents, plus from five to 500 percent molar excess.

* * * * *